United States Patent [19]
Ruoff et al.

[11] Patent Number: 5,547,748
[45] Date of Patent: Aug. 20, 1996

[54] CARBON NANOENCAPSULATES

[75] Inventors: Rodney S. Ruoff, Menlo Park; Donald C. Lorents, Palo Alto; Ripudaman Malhotra, San Carlos; Mark J. Dyer, San Jose, all of Calif.

[73] Assignee: SRI International, Menlo Park, Calif.

[21] Appl. No.: 182,283

[22] Filed: Jan. 14, 1994

[51] Int. Cl.$^6$ ....................................................... B32B 5/16
[52] U.S. Cl. .................. 428/323; 428/320.2; 428/328; 428/689; 423/439
[58] Field of Search ................................. 428/320.2, 323, 428/913, 195, 304.1, 328, 330, 689; 423/439

[56] References Cited

U.S. PATENT DOCUMENTS

| | | | |
|---|---|---|---|
| 5,196,396 | 3/1993 | Leeber | 505/1 |
| 5,223,479 | 6/1993 | McCanley, Jr. et al. | 505/1 |
| 5,294,602 | 3/1994 | Tanigaki et al. | 505/1 |
| 5,324,495 | 6/1994 | Gorlin | 423/439 |

OTHER PUBLICATIONS

Tomioka et al, Patent Abstract of Japan Grp No–C1133 vol. 17, No. 638.
Saito, Journal of Physics of Chemistry of Solids 1993 V54, N12.
Ajayan, P. M., et al., "Opening carbon nanotubes with oxygen and implications for filling", *Nature* 352:522–525 (1993).
Bethune, D. S., et al., "Atoms in carbon cages: the structure and properties of endohedral fullernes", *Nature* 366:123–128 (1993).
Birkett, P. R., et al., "Preparation and characterization of $C_{60}Br_6$ and $C_{60}Br_8$", *Nature* 357:479–481 (1992).
Chai, Y., et al., "Fullerenes with Metals Inside", *J. Phys. Chem.* 95:7564–7568 (1991).
Diederich, F., et al., "The Higher Fullerenes: Isolation and Characterization of $C_{76}$, $C_{84}$, $C_{90}$, $C_{94}$, and $C_{70}O$, and Oxide of $D_{5h}$–$C_{70}$", *Science* 252:548–551 (1991).

Ebbesen, T. W., and Ajayan, P. M., "Large–scale synthesis of carbon nanotubes", *Nature* 358:220–222 (1992).
Heath, J. R., et al., "Lanthanum Complexes of Spheroidal Carbon Shells", *J. Am. Chem. Soc. 107:7779–7780 (1985).*
Hirsch, A., "The Chemistry of Fullerenes: An Overview", *Angew. Chem. Int. Ed. Engl.* 32(8):1138–1141 (1993).
Hoke, S. H., II, et al., "Reaction of Fullerenes and Benzyne", *J. Org. Chem.* 57:5069–5071 (1992).
Iijima, S., "Helical microtubules of graphitic carbon", *Nature* 354:56–58 (1991).
Johnson, R. D., et al., "Electron paramagnetic resonance studies of lanthanum–containing $C_{82}$", *Nature* 355:239–240 (1992).
Kalsback, W. A., and Thorp, H. H., "Electrochemical reduction of fullerenes in the presence of $O_2$ and $H_2O$: Polyoxygen adducts and fragmentation of the $C_{60}$ framework", *J. Electroanal. Chem.* 314:363–370 (1991).
Majetich, S. A., et al., "Preparation and properties of carbon–coated magnetic nanocrystallites", *Physical Rev. B* 48(2):16845–16848 (1993).
Moro, L., et al., "Studies of Metallofullerene Primary Scots by Laser and Thermal Desorption Mass Spectrometry", *J. Phys. Chem.* 97:6801–6805 (1993).
Olah, G. A., et al., "Chlorination and Bromination of Fullerenes, Nucleophilic Methoxylation of Polychlorofullerenes and Their Aluminum Trichloride Catalyzed Friedel—Crafts Reaction with Aromatics to Polyarylfullerenes", *J. Am. Chem. Soc.* 113:9385–9387 (1991).

(List continued on next page.)

*Primary Examiner*—Patrick J. Ryan
*Assistant Examiner*—William A. Krynsley
*Attorney, Agent, or Firm*—Gary R. Fabian; Judy M. Mohr

[57] ABSTRACT

Encapsulation of metals inside multilayered polyhedral shells of carbon (nanoencapsulates) is described. Many materials, such as metals and metal-carbides, can be encapsulated by the method of present invention, including metals such as lanthanides, transition metals, actinides and alloys. Some of these nanoencapsulate materials exhibit ferromagnetic and paramagnetic properties and have uses in the biomedical field as well as in recording media and composite materials.

16 Claims, 13 Drawing Sheets

OTHER PUBLICATIONS

Ruoff, F. S., et al., "Single Crystal Metals Encapsulated in Carbon Nanoparticles", *Science* 259:346–348 (1993).

Seraphin, S., et al., "Yttrium carbide in nanotubes", *Nature* 362:503 (1993).

Seraphin, S., et al., "Insertion of Yttrium carbide into Carbon Nanoclusters by Vapor Transport During Growth", *Proc. 51st Ann. Mtg. Microscopy Soc. of America* (Bailey, G. W., et al., Eds.) San Francico Press (1993).

Subramoney, S., et al., "Radical single-layer nanotubes", *Nature* 366:637 (1993).

Taylor, R., "A Valence Bond Approach to Expaining Fullerene Stabilities", *Tetrehedron Lett.* 32:(30):3731–3734 (1991).

Taylor, R., et al., "Formation of $C_{60}Ph_{12}$ by Electrophilic Aromatic Substitution", *J. Chem. Soc. Chem. Commun.*, p. 667 (1992).

Taylor, R., "Rationalisation of the most Stable Isomer of a Fullerene $C_n$", *J. Chem. Soc. Perkin Trans.* 2:3–4 (1992).

Taylor, R., "The chemistry of fullerenes", *Nature* 363:685–693 (1993).

Tebbe, F. N., et al., "Multiple, Reversible Chlorination of $C_{60}$", *J. Am. Chem. Soc.* 113:9900–9901 (1991).

Tebbe, F. N., et al., "Synthesis and Single-Crystal X-Ray Structure of a Highly Symmetrical $C_{60}$ derivative, $C_{60}Br_{24}$"*Science* 256:822–824 (1992).

Tomita, M., et al., "$LaC_2$ Encapsulated in Graphite Nano-Particle", *Jpn. J. Appl. Phys.* 32:280–282 (1993).

Tsang, S. C., et al., "Thinning and opening of carbon nanotubes by oxidation using carbon dioxide", *Nature* 362:520–521 (1993).

Tuinman, A. A., et al., "Characterization and Stability of Highly Fluorinated Fullerenes", *J. Phys. Chem.* 96:7584–7589 (1992).

Wood, J. M., et al., "Oxygen and methylene Adducts of $C_{60}$ and $C_{70}$", *J. Am. Chem. Soc.* 113:5907–5908 (1991).

Wudl, F., et al., "Survey of Chemical Reactivity of $C_{60}$, Electrophile and Dieno-polarophile par Excellence" (Chapter 11) in *Fullerenes: Synthesis, properties, and Chemistry*, American Chemical Society (1992).

Yosida, Y., "Synthesis of $CeC_2$ crystals encapsulated within gigantic super fullerenes", *Appl. Phys. Lett.* 62(26):3447–3448 (1993).

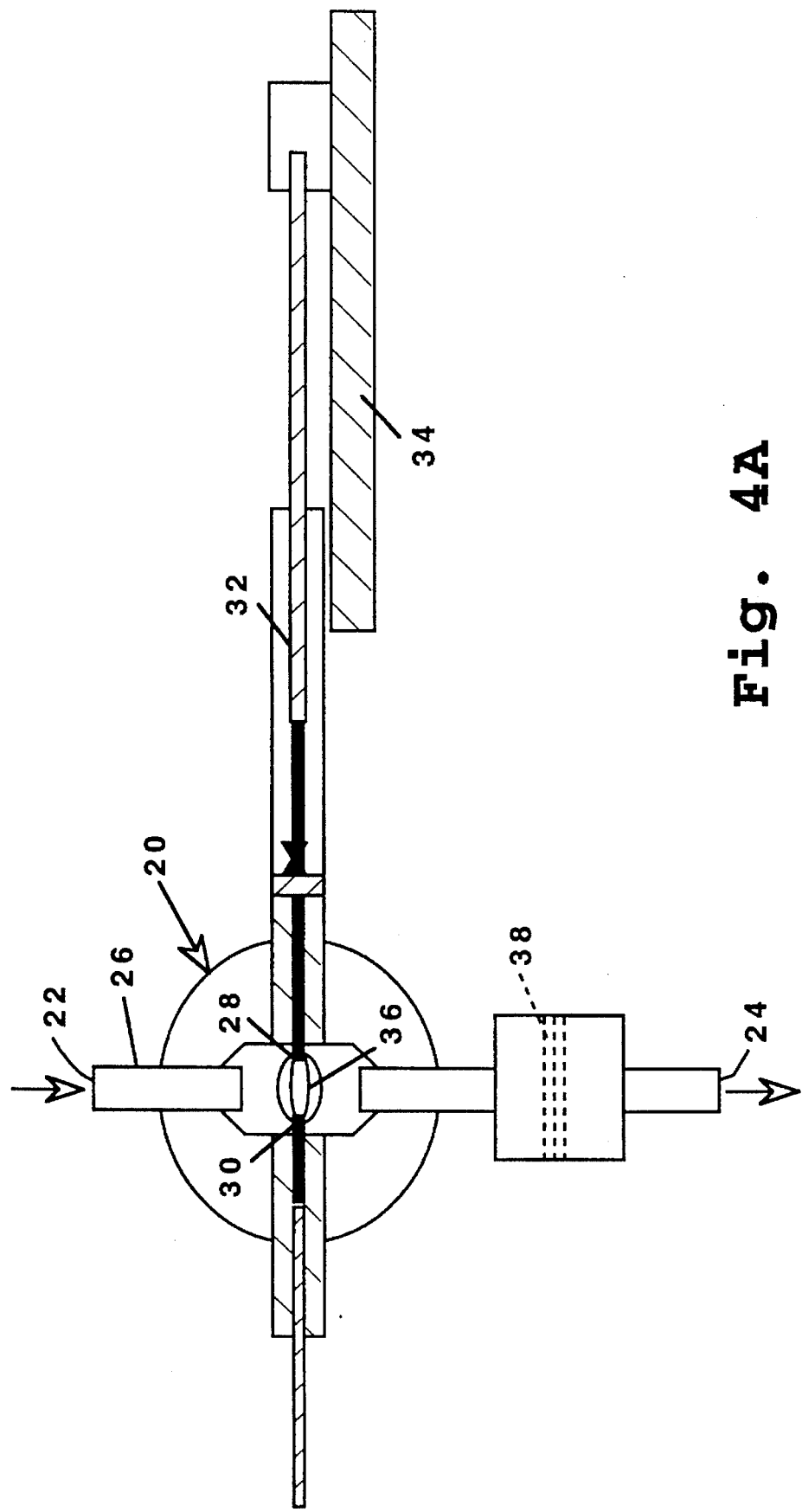

CARBON NANOENCAPSULATES

FIELD OF THE INVENTION

The present invention relates to carbon nanoencapsulates which are synthesized in a carbon-arc process. The nanoencapsulates are characterized by an outer carbon shell of nested concentric layers and an inner core of metal.

REFERENCES

Bethune, D. S., et al., *Nature* 366:123–127 (1993).
Birkett, P. R., et al., *Nature* 357:479–481 (1992).
Chai, Y., et al., *J. Phys. Chem.* 95:7564 (1991).
Diederich, F., et al., *Science* 252:548–549 (1991).
Ebbesen, T. W., et al., *Nature* 358:220 (1992).
Heath, J. R., et al., *J. Am. Chem. Soc.* 107:7779 (1985).
Hirsch, A., *Angew. Chem. Int. Ed. Engl.* 32:1138–1141 (1993).
Hoke, S. H., et al., *J. Org. Chem.* 57:5069–5071 (1992).
Iijima, S., *Nature*, 354, 56 (1991).
Johnson, R. D., et al., *Nature* 355:239 (1991).
Kalsbeck, W. A., et al., *J. Electroanal. Chem.* 314:363–365 (1991).
Lallement, *U.S. Dept. Com., Clearinghouse Sci. Tech. Inform.* AD 627224:11, (1965).
Moro, L., et al., *J. Phys. Chem.* 97:6801–6805 (1993).
Olah, G. A., et al., *J. Am. Chem. Soc.* 113:9385–9387 (1991).
Papaspyrou, M., et al., *Nucl. Sci. Eng.* 110:349–354 (1992).
Spedding, F. H., et al., *J. Am. Chem. Soc.*, 80, 4499 (1958).
Stomp, A. M., et al., U.S. Pat. No. 5,122,466, issued 16 Jun. 1992.
Taylor, R., et al., *Tetrahedron Lett.* 3731–3734 (1991).
Taylor, R., et al., *J. Chem. Soc. Chem. Commun.*, 667–668 (1992a).
Taylor, R., et al., *J. Chem. Soc. Perkin Trans.* 2, 3–4 (1992b).
Taylor, R., et al., *Nature* 363:685–692 (1993).
Tebbe, F. N., et al., *J. Am. Chem. Soc.* 113:9900–9901 (1991).
Tebbe, F. N., et al., *Science* 256:822–825 (1992).
Tenne, R., et al., *Nature* 360:444 (1992).
Tersoff, *J. Phys. Rev. B*, 46, 546 (1992).
Tuinman, A. A., et al., *J. Phys. Chem.* 96:7584–7589 (1992).
Wood, J. M., et al., *J. Am Chem. Soc.* 113: 5907–5908 (1991).
Wudl, F., et al., Chapter 11, "Survey of Chemical Reactivity of $C_{60}$, Electrophile and Dienopolarophile Par Excellence," in *Fullerenes: Synthesis, Properties, and Chemistry*, American Chemical Society, 1992.

BACKGROUND OF THE INVENTION

Fullerenes are a family of closed-cage molecules formed entirely of carbon in the $sp^2$-hybridized state and constitute the third form of carbon after diamond and graphite. These spherical, cavity-containing molecules have been found to possess novel, remarkable properties, and the buckminsterfullerene $C_{60}$ has been widely investigated (Hirsch; Taylor, 1993).

Fullerenes are produced in a carbon-arc process where an inert gas flows through a reaction vessel at a controlled pressure. A potential, either a.c. or d.c., is applied between two graphite rods in the vessel, where one rod can be smaller in diameter than the other. As the rods are brought close together, a discharge occurs resulting in the formation of a carbon plasma. As the smaller rod is consumed, the rods are kept at a constant distance from each other of approximately 1–5 mm. The electric current depends on the size of the rods, their separation, the gas pressure, and other parameters, but typically it is about 100 A (Ebbesen).

At the extremely high temperatures in the plasma of the carbon-arc process where fullerenes are synthesized, a variety of by-products are also synthesized. The first recognized by-products were nested carbon tubes and polyhedra (Iijima), the discovery of which extended the dimensions and geometries of fullerenes into the nanometer domain.

Exohedral and endohedral modifications to fullerenes, in particular to the easily accessible $C_{60}$, have been reported (Hirsch; Taylor, 1993; Heath; Chai; Johnson; Moro). Exohedral modifications of fullerenes by addition reactions have shown $C_{60}$ to be reactive, and derivatives of fullerenes have been produced (Bethune, Hirsch). Endohedral modifications involve deposition of atoms into the cavity within the cage. Helium, other noble gas atoms, and metal atoms have been incorporated in fullerenes (Bethune).

SUMMARY OF THE INVENTION

The invention includes a nanoencapsulate where a metal is encapsulated in a nanopolyhedron. This nanoencapsulate has a polyhedral outer shell of nested, concentric layers of carbon, which defines an internal cavity or void. Encapsulated within this cavity is a metal.

Preferably, the outer diameter of the nanoencapsulate is between 5 nm and 1000 nm. More preferably, the outer diameter is between 10 nm and 500 nm.

The outer diameter of the nanoencapsulate can be adjusted after synthesis by controlled oxidation or by chemical digestion of a nanoencapsulate of a larger size. Controlled oxidation can be used to consume the outermost layers of the nanoencapsulate, thereby reducing the outer diameter of the nanoencapsulate. For example, exposure of the nanoencapsulate to elevated temperatures of, for instance, 500°–600° C., in an oxygen-containing environment results in oxidation of the carbon, giving by-products such as carbon monoxide and carbon dioxide. In this manner, the outer carbon shell of the nanoencapsulate is consumed, resulting in a reduction in nanoencapsulate dimensions.

A variety of elements can be encapsulated within the nanopolyhedra, including elements from the actinide series, such as uranium, and elements from the lanthanide series, such as La and Gd.

Paramagnetic and ferromagnetic elements, such as Fe, Co, Ni, can also be encapsulated. In another embodiment, the ferromagnetic metal Gd is encapsulated in its dicarbide form to give a paramagnetic nanoencapsulate. Alternatively, a paramagnetic metal may be encapsulated to give a paramagnetic nanoencapsulate, or a ferromagnetic metal may be encapsulated to give a ferromagnetic nanoencapsulate.

The metal, in another embodiment, is an alloy. The alloy may be two or more transition elements or the carbide form of such an alloy, either crystalline or amorphous. The alloy may also be a mixture of a transition element and a rare earth element, or the carbide form of such an alloy, either crystalline or amorphous. A preferred alloy is Sm—Co.

In other embodiments, the carbon shell of the nanoencapsulate is derivatized with a molecule. For example, the corners of the carbon shell, which are likely reactive, are covalently modified with appropriate functional groups.

In another aspect, the invention includes a method of making a nanoencapsulate between two graphite rods in a carbon-arc discharge process. In this process the central bore of a first graphite rod is filled with a metal or a metal compound and the carbon-arc process is run under conditions where a deposit or boule forms on one of the graphite rods and a soot is also produced as a co-product. The nanoencapsulates are recovered from the deposit and/or the soot.

A ferromagnetic metal encapsulated in the nanopolyhedra will form magnetic nanoencapsulates, which can be recovered, or separated from other products in the carbon-arc process, by magnetic extraction, such as with a magnet.

In another aspect, the invention includes an encapsulate, which has a central core of metal. A plurality of single layer carbon nanotubes extend radially outward from the metal core and are arranged around the outer surface of the core.

These and other objects and features of the invention will be more fully appreciated when the following detailed description of the invention is read in conjunction with the accompanying drawings.

BRIEF DESCRIPTION OF THE DRAWINGS

FIGS. 4A and 4B show a schematic of an apparatus for producing nanoencapsulates, where FIG. 4A illustrates a single-arc process and FIG. 4B shows a multi-arc process;

DETAILED DESCRIPTION OF THE INVENTION

A. Definitions

As used herein, the term "nanopolyhedra" refers to carbon polyhedra composed of nested, concentric layers of carbon, where the layers are composed largely of hexagons and pentagons, and the polyhedra typically have dimensions on the order of nanometers to hundreds of nanometers.

As used herein, the term "nanoencapsulates" refers to carbon nanopolyhedra encapsulating a material, such as a metal or a metal carbide, which fills or partially fills the innermost voids of the nanopolyhedra.

The term "metal" is defined herein to include (i) pure elemental metals, (ii) combinations of pure elemental metals with carbon to give a carbide, either crystalline or amorphous, and (iii) alloys or carbides thereof.

B. Description of Nanoencapsulate

The by-products that are synthesized in the carbon-arc process, as described above, include small graphitic particles, amorphous carbon, and, in particular, polyhedral particles.

Figure 1:
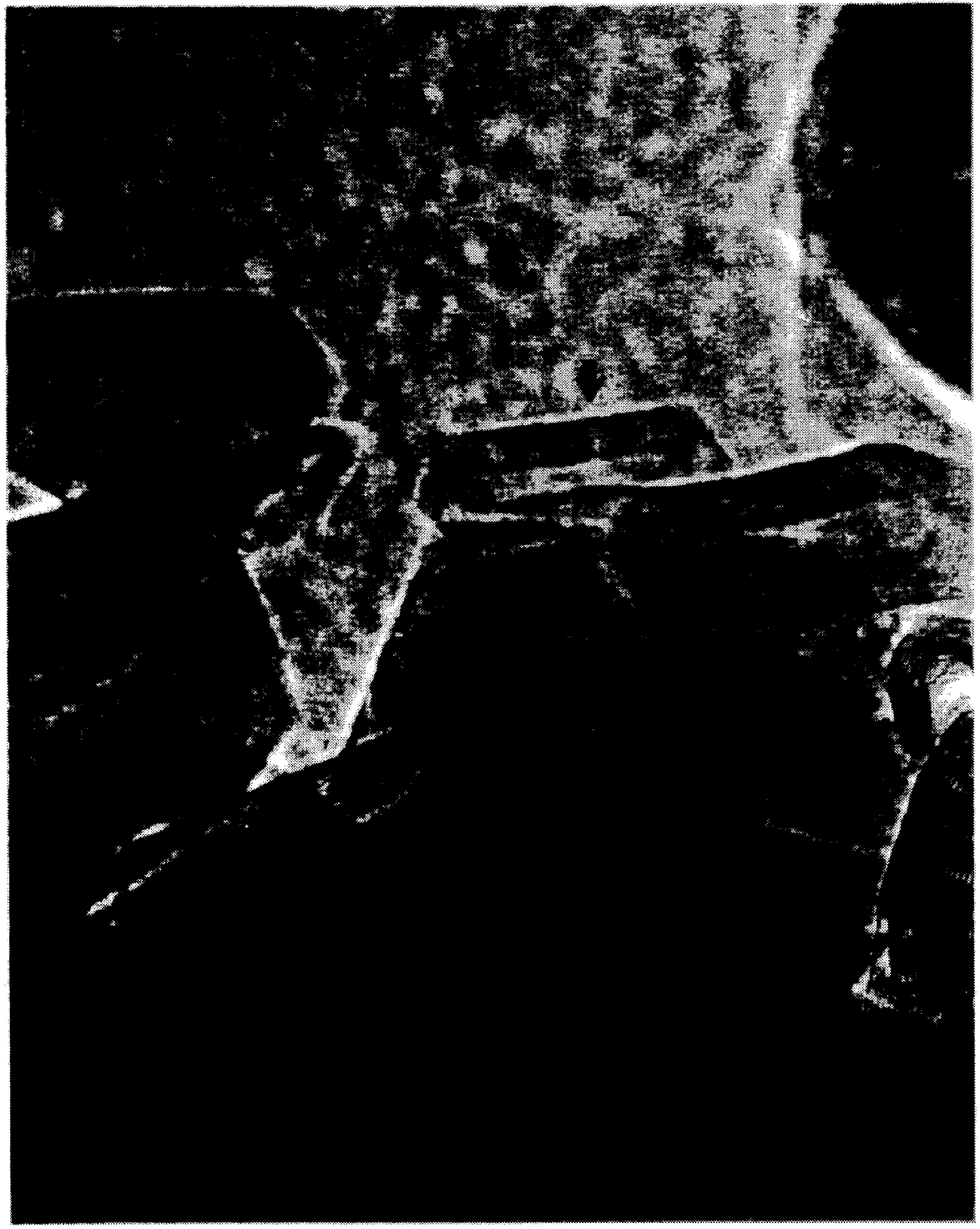
FIG. 1 is a high resolution transmission electron microscope (HRTEM) image of carbon nanopolyhedra.

FIG. 1 is a high resolution transmission electron microscope (HRTEM) image of polyhedral particles, or nanopolyhedra. Like fullerenes, these nested polyhedra consist of hexagons and achieve closure by inclusion of twelve pentagons, however, fullerenes typically contain on the order of 100 carbon atoms, whereas, nanopolyhedra contain on the order of $10^5$ carbon atoms. Important features of the nanopolyhedra include the well replicated nested structure and the internal cavity. The oblong polyhedron indicated by the arrow in FIG. 1 has nine layers of nested carbon and is approximately 9 nm wide and 27 nm long.

According to an important aspect of the invention, it was recognized that the internal cavities of these structures, that is, the nanopolyhedra, could be filled with a selected element, such as La or Gd, during the carbon arc process by packing one of the graphite rods with the selected element.

Figure 2:
FIG. 2 is a HRTEM image showing the various types of particles formed during synthesis of nanoencapsulates in a carbon-arc discharge process.

Experiments performed in support of this invention where the anode rod in the carbon-arc process was packed with La$_2$O$_3$, as described in Example 1A, yielded the particles shown in FIG. 2. These particles are in the 5–1000 nm range and include a multifaceted polyhedron, indicated at 1 in FIG. 2, with on outer diameter of approximately 33 nm.

Also seen in FIG. 2 is a small piece of amorphous carbon, indicated as particle 2. Particle 3 is a nanotube with a diameter of approximately 16 nm, and particle 4, to be described below, is a nanoencapsulate of $\alpha$-LaC$_2$ with an outer diameter of approximately 53 nm and an inner diameter of approximately 28 nm.

Experiments done in support of this invention have demonstrated that a variety of metals can be encapsulated in the cavity of a nanopolyhedron. These metals include, but are not limited to, the following elements, alloys, and carbides thereof: actinide series elements (Ac, Th, Pa, U, Np, Pu, Am, Cm, Bk, Cf, Es, Fm, Md, No, Lr), lanthanide series elements (La, Ce, Pr, Nd, Pm, Sm, Eu, Gd, Tb, Dy, Ho, Er, Tm, Yb, Lu), ferromagnetic elements such as Fe, Co, Ni, Gd, paramagnetic elements, alkaline earth carbides (such as CaC$_2$), elemental alloys (Sm—Co) and transition element alloys, such as iron-rich transition element alloys (FeV, FeCr, FeNi, FeCo) cobalt-rich transition element alloys (CoCr, CoNi) nickel-rich transition element alloys (NiCr, NiV), and iron-rich rare earth alloys, such as $R_2Fe_{17}$ (where R=Ce, Pr, Nd, Sm, Gd, Tb, Dy, Er, Y).

In support of the present invention, metals from the lanthanide family, such as La and Gd, have been encapsulated in the carbide form. Uranium, from the actinide family, has also been encapsulated as uranium dicarbide. Other ferromagnetic materials, in addition to Gd, have been encapsulated, including Fe and Ni. The alloy Sm—Co has also been encapsulated.

Figure 3A:
FIGS. 3A–3C are HRTEM images of nanoencapsulates, where the internal cavities of the nanopolyhedra are partially filled with $\alpha$-LaC$_2$ (FIG. 3A), $\alpha$-GdC$_2$ (FIG. 3B) and UC$_2$ (FIG. 3C)

Example 1A describes the carbon-arc process for the synthesis of $LaC_2$ nanoencapsulates. FIG. 3A is a HRTEM image of a nanoencapsulate with its internal cavity partially filled with $\alpha$-$LaC_2$. There are about 30 carbon layers in the shell of the nanoencapsulate, and the layer spacing between them is 3.42Å. The fringe spacing between the planes in the $LaC_2$ is 3.39Å, which corresponds to the spacing in the (101) plane of $\alpha$-$LaC_2$. The crystal boundaries of the $\alpha$-$LaC_2$ conform to the interior carbon shell walls, which suggests that the particle is completely enclosed within the carbon nanoparticle.

$\alpha$-$LaC_2$ has the crystal structure of $CaC_2$ and is the room temperature stable phase of $LaC_2$. $LaC_2$, like $CaC_2$, rapidly undergoes oxidation to $La_2O_3$ and acetylene, with minor amounts of other hydrocarbons. The $LaC_2$ nanoencapsulates were exposed to air for several days prior to HRTEM analysis and showed no evidence of oxidative degradation, which suggests that the $\alpha$-$LaC_2$ is protected from oxidation by the multilayered carbon nanoparticle cage.

Figure 3B:
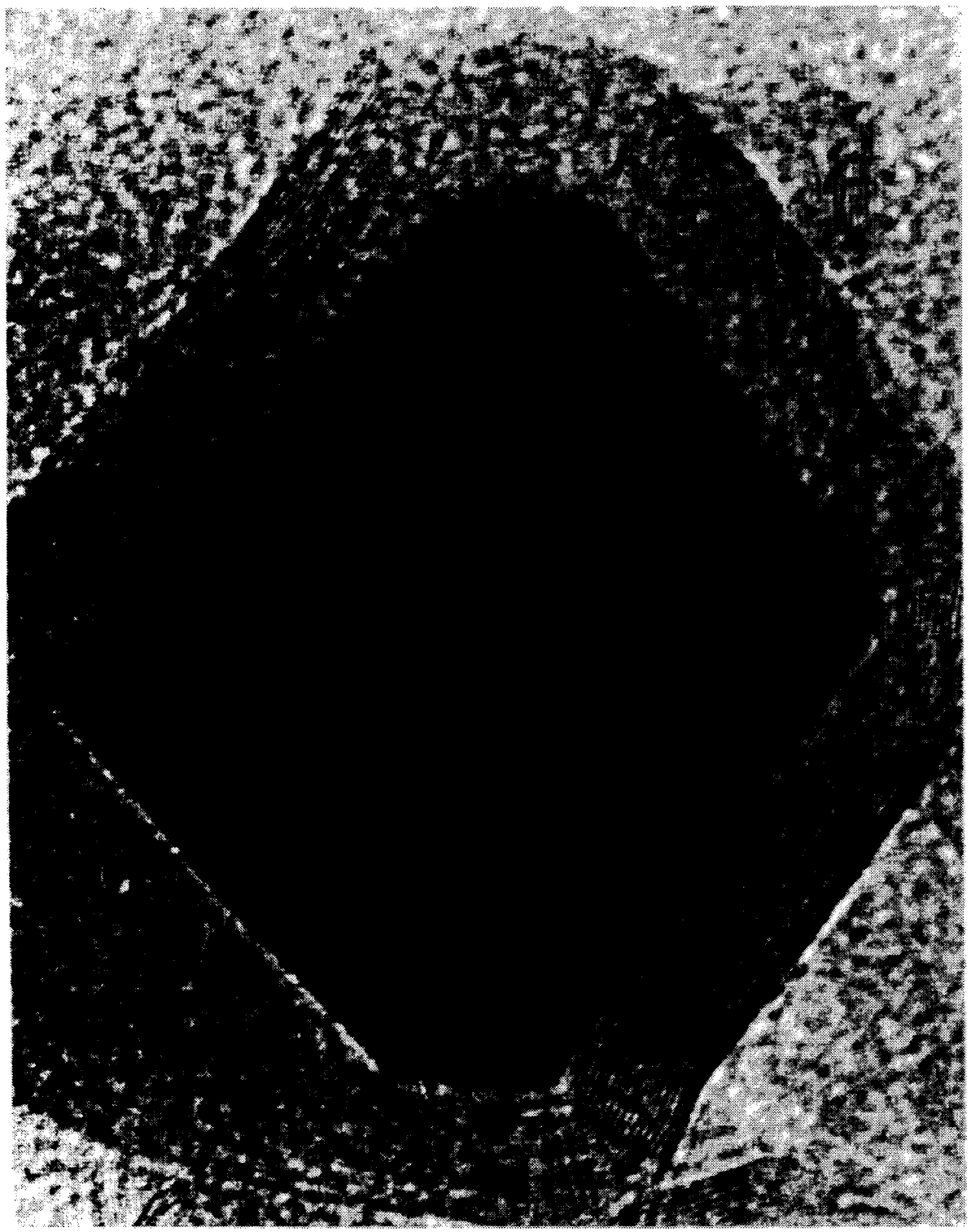

Example 1B describes the synthesis of $GdC_2$ nanoencapsulates. These nanoencapsulates were characterized as follows. FIG. 3B is a HRTEM image of a nanoencapsulate where $\alpha$-$GdC_2$ is encapsulated inside a carbon nanopolyhedron, synthesized as described in Example 1B. The diameter of the outermost carbon polyhedron is approximately 50 nm. It is also apparent in the image that the entire cavity of the innermost carbon polyhedron is not completely filled by the $\alpha$-$GdC_2$.

Identification of the carbide form of Gd encapsulated was made by taking accurate measurements of the lattice fringe spacings from several high resolution images of the nanoencapsulates. The spacings matched well with the interplanar spacings of the (101), (002), and (110) planes of $\alpha$-$GdC_2$. Further verification of the phase of the encapsulated metal was obtained by measurement of the angles of different sets of fringes, which matches very well with those from theoretical calculations for tetragonal crystals.

As described below, the $\alpha$-$GdC_2$ nanoencapsulates were also examined by X-Ray Diffraction (XRD; Example 2) and Energy Dispersive Spectroscopy (EDS). These analyses demonstrated that only Gd and C were present. No characteristic peaks of oxygen were evident.

Figure 3C:

Example 1C describes the synthesis of $UC_2$ nanoencapsulates. FIG. 3C is a HRTEM image of a $UC_2$ nanoencapsulate synthesized in a carbon-arc process. As seen here, the $UC_2$ fills nearly the entire inner cavity of the innermost polyhedron. The long axis length, or largest diameter, of the $UC_2$ nanoencapsulate is approximately 60 nm, and other $UC_2$ nanoencapsulates with average diameters of 100 nm have been obtained.

The results described above demonstrate the ability to synthesize nanoencapsulates having a variety of inner core materials, such as metals and the carbide form of metals, in both crystalline and amorphous forms.

An apparatus for producing the nanoencapsulates in accordance with the invention is shown schematically in FIG. 4A. Seen here is a single-arc apparatus consisting of a reaction chamber 20 formed of a suitable material, such as stainless steel. An inert gas, such as helium or argon, flows through the chamber entering at port 22 and exiting at port 24, which is attached to a vacuum pump.

A cylindrical tube 26, positioned in the center of the chamber, runs the length of the reaction vessel and is temperature controlled with cooling coils (not shown).

Two electrodes 28, 30 are positioned within the reaction chamber, where electrode 28 is the anode and electrode 30 is the cathode. The anode is attached to a translating rod 32 which is mounted on a geared translation stage 34.

Under appropriate conditions of pressure, temperature, potential and electrode distance, a discharge or arc 36 between the two electrodes occurs, resulting in the formation of a plasma. During this process, the anode, which is packed with the metal or metal compound to be encapsulated, is consumed. The distance between the electrodes is maintained using the translating rod and stage apparatus.

Packing the anode rod is accomplished by drilling out the center of the rod, as described in Example 1A. The central bore is filled with a metal or a metal compound, such as metal oxide, metal halide, metal nitride, or metal chalcogenide, including dichalcogenides. Other metal compound compositions that contain the element of interest, such as organometallics, are suitable for packing into the anode rod.

A carbonaceous deposit or boule forms on the cathode 30, which contains, along with other products, the nanoencapsulates. A soot material is also formed, which is collected on a filter 38 and may also contain nanoencapsulates along with other products.

Figure 4B:
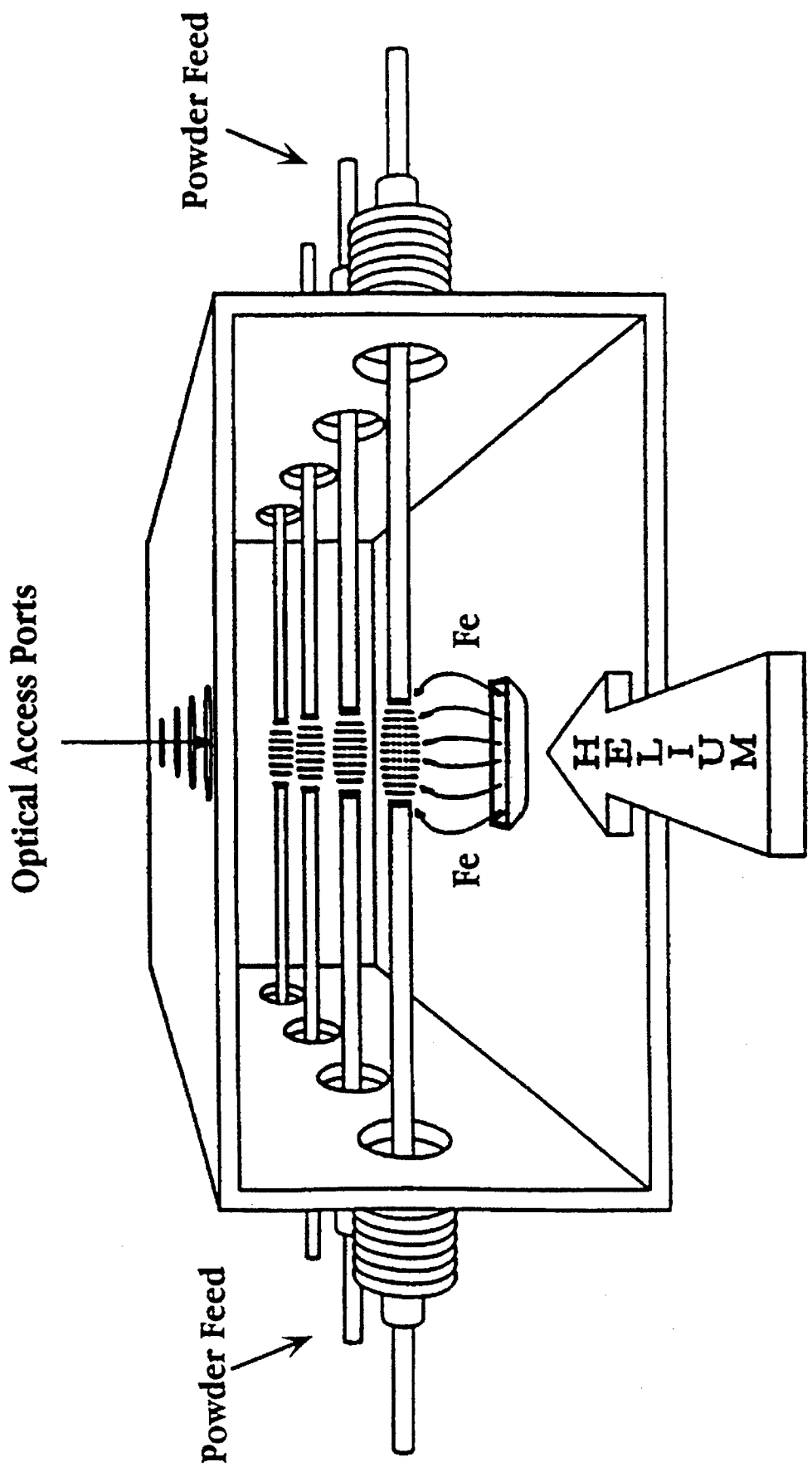

Alternative synthesis schemes may lead to novel new encapsulates or allow encapsulation of elements that may not be encapsulated in the high temperature environment of a standard fullerene chamber arc. An apparatus useful in such an alternative synthesis scheme is presented in FIG. 4B. FIG. 4B shows a schematic of a multi-arc apparatus for producing nanoencapsulates. Electrodes can be graphite and a variety of metals or alloys. Sublimation sources allow introduction of atomic and cluster vapors for mixing with arc-produced species. Sample ports (not shown in FIG. 4B) allow sampling of products at different locations.

By controlling the relative positions of the separate arcs and sublimation sources, it will be possible to expose a wide variety of small metal clusters to a gaseous carbon environment. Further, encapsulation studies need not be limited to carbon-coating. With such a device, nanoencapsulates may be generated with a variety of other coatings, for example, analogues of graphite, such as $MoS_2$ or $WS_2$. Recently synthesis of nanopolyhedral structures similar in appearance to the carbon nanopolyhedra have been generated that are comprised of $WS_2$ rather than C (Tenne, et al., 1992).

The instrument shown in FIG. 4B can be designed so that fluorescence and laser diagnostics can be performed on the arc and inter-arc regions. This new synthesis instrument will likely allow the production of new types of carbon-coated encapsulates, particularly magnetic encapsulates.

C. Characterization of Nanoencapsulates

1. Extraction. The nanoencapsulates synthesized in the carbon arc process can be separated from the other by-products, such as amorphous carbon, by a variety of techniques.

A variety of methods may be useful to improve the purity of the nanoencapsulates. As briefly mentioned above, the present production technique leads to a mixture of carbon-coated nanoencapsulates, empty carbon polyhedra, and amorphous and graphitic carbon debris. One method to improve purity of nanoencapsulates may be preferential chemical digestion of the carbon debris with different oxidants: for example, thermal oxidation as a method for removing the debris material. Thermal gravimetric analysis was performed to, e.g., 50% mass loss by thermal oxidation. Subsequent analysis of the sample by transmission electron microscopy showed that the amorphous and graphitic carbon debris was preferentially removed, due to higher reactivity.

Preliminary results indicate that these methods leave a mixture which contains both empty and nanoencapsulating carbon polyhedra, but is free of amorphous carbon particles. Separation techniques based on density may also allow separation of the nanoencapsulates from the non-encapsulates.

Magnetic nanoencapsulates can be magnetically separated. For example, nanoencapsulates of $\alpha$-$GdC_2$ and of carbides of Co, Fe, and Ni, have all been separated using a hand-held $SmCo_5$ magnet. Another simple technique has been to magnetize a razor blade and pull magnetic particles by hand, exploiting the strong gradient field present at the razor tip. Magnetic extraction techniques can be automated based on gradient magnetic fields. Flow entrainment techniques may also be used in conjunction with magnetic separation.

Alternatively, conventional chemical means could be employed, where differences in the solubilities or the dielectric constants of the by-products enable separation. The density of the nanoencapsulates will differ from the other by-products, and this difference can be utilized for separation by centrifugation.

Encapsulation of a ferromagnetic or paramagnetic elements allows for magnetic extraction, where the nanoencapsulates filled with the magnetic element can be separated from those that are not filled by use of a magnetic gradient field.

2. Structure. The nanoencapsulates shown in FIGS. 3A–3C are characterized by nested polyhedral shells. The nanoencapsulate has flat sides, joined at angles of about 45° to 90°. The faceted hollow polyhedral particles are giant nested fullerenes: closed structures with 12 pentagons in the hexagonal graphitic lattice. Exact replication of layer geometry in the polyhedra suggests a growth process that duplicates underlying layers including pentagon positions. Models of these structures clearly demonstrate the roles of pentagon placement in symmetric and asymmetric polyhedra.

In the case of the very symmetric (nested) polyhedra, such as the pentahedron, it can be simply demonstrated that these particles have the ABAB . . . layer structure like that of graphite. The particle geometry is constrained by the hexagon dimensions to an interlayer spacing of 0.34–0.35 nm, which is larger than the graphitic stacking. In the case of the pentahedron the ABAB . . . stacking was demonstrated by construction of a properly scaled nested model. However, a simple calculation of the perimeters within the constraint of integral number of hexagons is equally convincing. The difference in the triangular perimeters of two adjacent pentahedra, assuming they are equilateral triangles with corners that are of equal radii of curvature, is $$\Delta l = a\Delta n = 2d\{\tan(\pi/6) + \sec(\pi/6)\} = 3.46d$$

where a=2.46Å is the graphite hexagonal dimension, $\Delta n$ is the difference in the number of hexagons in the two layers and d is the layer spacing. Since d=3.5±0.1Å, $\Delta n$, which must be an integer, is 5. The odd number clearly implies ABAB . . . stacking. Although the van der Waals forces between layers may alter the covalent bond lengths and the hexagonal dimension slightly, a very large change would be required to alter this conclusion. For rectangular polyhedra, similar arguments lead to ABAB . . . stacking with $\Delta n=3$. However, for pentagonal and hexagonal geometries, the graphite stacking condition is not consistent with the observed d spacing. Such particles have geometries approaching that of a tube and are expected to have non-commensurate layers.

Figure 5:
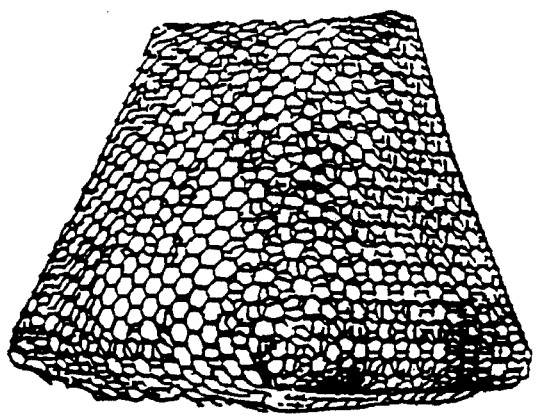
FIG. 5 is a model of a pentahedral nanopolyhedron constructed with plastic vugraph material imprinted with a hexagonal lattice.

A model of a pentahedral nanopolyhedron was created from vugraph sheets imprinted with a hexagonal lattice and is shown in FIG. 5. The model illustrates how the paired pentagons shape the corners and also shows the sharp bends required of the hexagonal lattice at the edges. This method of producing models is based on the inextensional elastic distortion of a graphene sheet, which has been shown to be an excellent approximation for the modelling of fullerene geometries (Tersoff) and it should be valid for giant fullerenes, like the carbon nanoencapsulates of the present invention.

In the pentahedral model shown in FIG. 5, the corner pentagons are separated by a single hexagon which corresponds to the sharp corners indicated in the innermost pentagon of the nanoencapsulates. In the outer pentahedra of the nanoencapsulates, the corner pentagons are separated by several hexagons which creates an additional facet.

An important feature of the faceted nanopolyhedra and nanoencapsulates are the sharp bends of the hexagonal lattice required between the polyhedral geometries. In the pentahedron case, $\pi/2$ bends are required at the edges of the rectangular faces. These sharp bends introduce strain energy which is inversely proportional to the square of the radius of curvature. The bending radius in this case appears to be on the order of 2–3 ring diameters. The strain at the bends, or corners, results in these areas being more reactive than the flat sides of the pentahedron.

The high degree of replication of the layers of this particle in spite of the strain shows that the pentagons are in the same relative position in each layer. The excellent replication also suggests that the growth process begins with a single template which was then replicated by either inward or outward addition of layers.

The presence of pentagons is the key to the reactivity of simple fullerenes such as $C_{60}$ and $C_{70}$ (Taylor, 1991, 1992b). The pentagons introduce strain in the system and makes possible a variety of nucleophilic, radical, and electrophilic addition reactions. As mentioned above, an important feature of the carbon nanoencapsulates is the sharp corners, which are likely to be reactive.

Similarly, nanoencapsulates may be reactive at the strained corners, enabling the nanoencapsulate to be derivatized or functionalized with a variety of molecules. Reactions that might be suitable for derivatizing these encapsulates include nucleophilic addition of amines, thiols, and carbanions; radical additions with halogens ($Cl_2$, $Br_2$, etc.), mixed halogens (ICl, IBr, etc.), and nitrogen oxides, alkyl, aryl and aralkyl radicals; cycloadditions with carbenes and dipolar species like diazoalkanes. Chemical modification of nanoencapsulates will be useful for changing their physical properties such as solubility to enable purification, and for attaching other chemically and/or biochemically active species. In the latter case, the specific activity of the attached moiety (drug, antibody, or chromophore, etc.) is of interest and the nanoencapsulate serves as a useful vehicle for delivery.

3. Composition. The $\alpha$-$LaC_2$, $\alpha$-$GdC_2$ and $UC_2$ nanoencapsulates were examined by X-Ray Diffraction (XRD), as described in Example 2, and by energy dispersive spectroscopy (EDS).

Figure 6A:
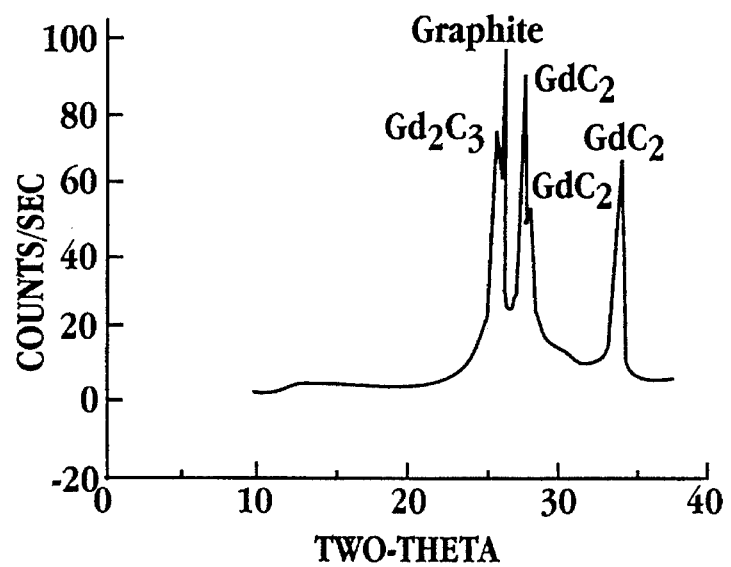
FIGS. 6A–6B are X-Ray Diffraction (XRD) patterns for nanoencapsulates of $\alpha$-GdC$_2$ prior to (FIG. 6A) and after (FIG. 6B) magnetic purification.
Figure 6B:
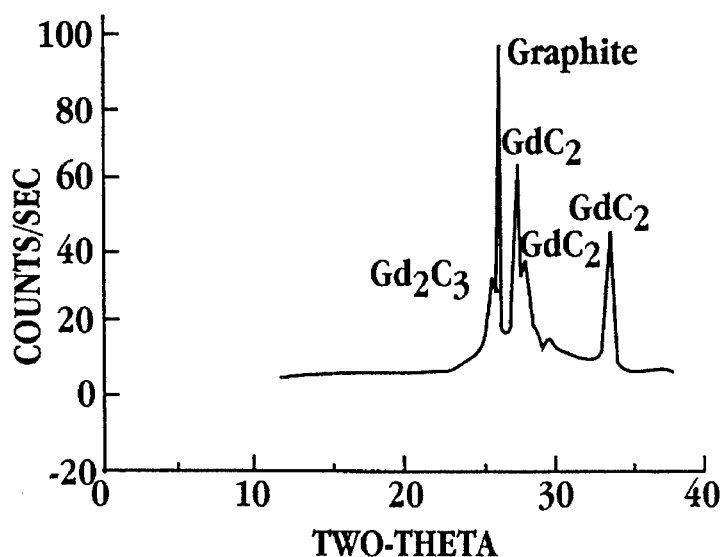

FIGS. 6A and 6B show XRD patterns for $\alpha$-$GdC_2$ nanoencapsulates before (FIG. 6A) and after (FIG. 6B) magnetic extraction. FIG. 6A shows the presence of $\alpha$-$GdC_2$ as well as a significant amount of $Gd_2C_3$. The peak corresponding to graphite seen at 26 (two-theta) degrees is primarily due to the carbon shells of the polyhedra. FIG. 6B, taken after exposing the sample to a magnetic field, shows that $\alpha$-$GdC_2$ is the component primarily extracted, as it has a larger magnetic moment per unit mass than $Gd_2C_3$. This result demonstrates the ability to separate nanoencapsulates of ferromagnetic or paramagnetic elements by magnetic extraction: the nanoencapsulates containing the magnetic element can be largely separated from those that do not contain the element by using a magnetic field gradient.

XRD of the $\alpha$-$LaC_2$ nanoencapsulates showed four characteristic d spacings of 2.800Å, 2,136Å, 1.980Å and 1.925Å. These spacings agree well with the reported spacings in the literature (Spedding).

Elemental analysis was performed with a high-angle Noran energy dispersive spectroscopy analyzer with a Be window and Ge detector. For specific identification of the composition of low Z materials in the carbon nanoencapsulates, namely oxygen, a Phillips CM-30 TEM equipped with a windowless Link EDS analyzer was used.

For the $\alpha$-$LaC_2$ nanoencapsulates, the EDS spectrum exhibited the characteristic peaks associated with La, and an EDS spectrum obtained with the windowless detector clearly showed the presence of only carbon and La. No characteristic peaks of oxygen were evident.

Similar results were obtained for EDS spectra of $\alpha$-$GdC_2$ nanoencapsulates. Namely, carbon and Gd were the only detected elements, and no peaks characteristic of oxygen were observed.

Both $\alpha$-$LaC_2$ and $\alpha$-$GdC_2$ are hydrolyzed by the moisture in air. The nanoencapsulates of these dicarbides were analyzed by TEM and XRD as a function of time to check for degradation by hydrolysis. For $\alpha$-$GdC_2$ nanoencapsulates, TEM images showed no evidence of degradation and the XRD patterns had no oxygen peaks. The stability of the $\alpha$-$LaC_2$ nanoencapsulates and the $UC_2$ nanoencapsulates were monitored over a 4 month period and showed no evidence of oxidation or hydrolysis. This data suggests that the metals are protected by the multilayered carbon nanoparticle and can be said to be completely encapsulated.

A vibrating sample magnetometer was used to study the magnetic nature of the $\alpha$-$GdC_2$ nanoencapsulates over the temperature range 4.2–300K and the magnetic field range −10 KOe to +10 KOe, as described in Example 3.

Figure 7A:
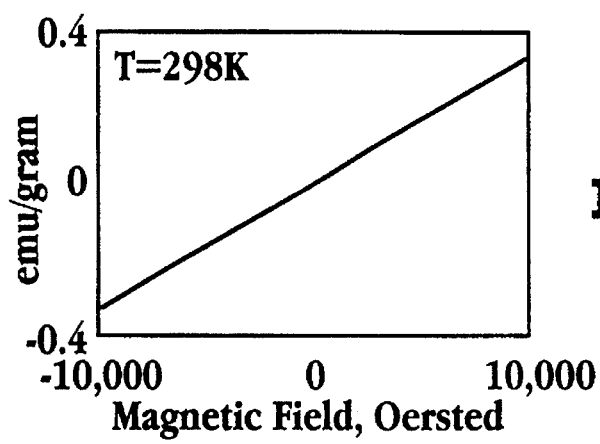
FIGS. 7A–7B are magnetization curves of magnetic susceptibility, in emu/gram, as a function of applied magnetic field, in Oe, for $\alpha$-GdC$_2$ nanoencapsulates prior to (FIG. 7A) and after (FIG. 7B) magnetic purification.
Figure 7B:
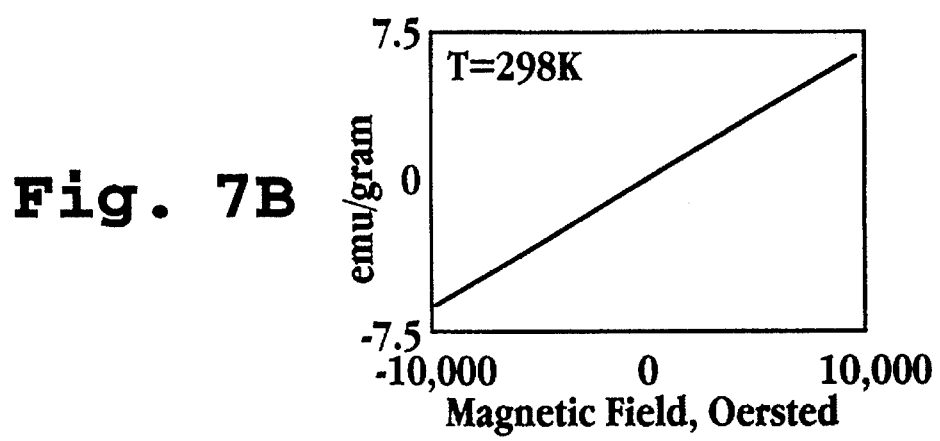

The dependence of the magnetic moment, emu/gram, of the $\alpha$-$GdC_2$ nanoencapsulates on an external field, from −10 to 10 KOe, was measured at 298K, as shown in FIGS. 7A and 7B. FIG. 7A is a sample of $\alpha$-$GdC_2$ nanoencapsulates taken prior to magnetic extraction, and FIG. 7B is the sample after magnetic extraction at room temperature with a 5 kG samarium cobalt magnet.

Seen in FIGS. 7A and 7B, the dependence of the magnetic moment on an external field is linear with a positive slope over the entire field, which demonstrates that the $\alpha$-$GdC_2$ nanoencapsulates are paramagnetic. Magnetic extraction resulted in a 20-fold increase in the concentration of the paramagnetic component, as seen in comparing the magnetic moment values in emu/gram of FIGS. 7A and 7B.

Figure 8:
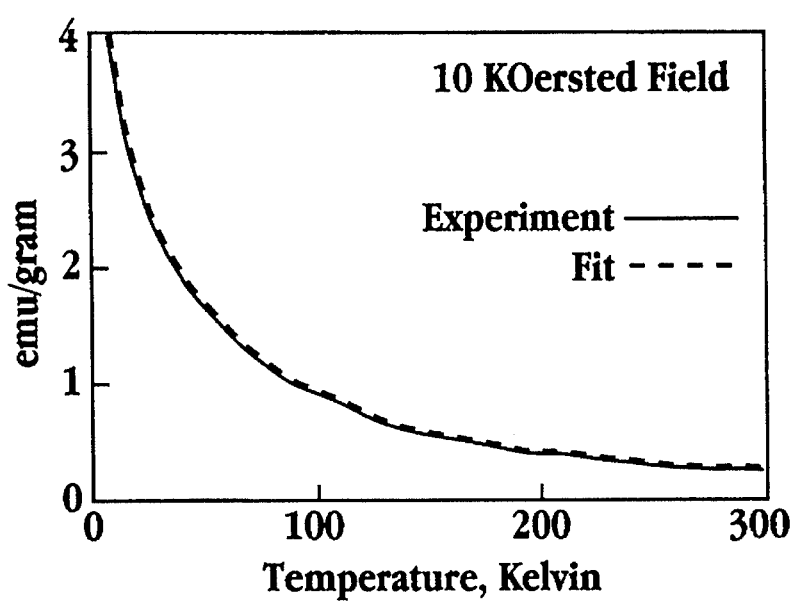
FIG. 8 shows the measured and calculated magnetic susceptibility, in emu/gram, as a function of temperature, in Kelvin, for a $\alpha$-GdC$_2$ nanoencapsulate.

Temperature dependent magnetic moment data for the $\alpha$-$GdC_2$ nanoencapsulates over the range 4 to 300K is shown in FIG. 8. Based on the XRD analyses, the paramagnetic response of the gadolinium-carbide nanoencapsulates appears to be the result of gadolinium dicarbide, $\alpha$-$GdC_2$, which in bulk form has an antiferromagnetic transition temperature of 42K (Lallement). As seen, in FIG. 8, a clear antiferromagnetic transition temperature at 42K is not observed for the $\alpha$-$GdC_2$ nanoencapsulates. The nanoencapsulates follow the Curie law dependence on reciprocal temperature down through the transition temperature of 42K, and are thus considered to be superparamagnetic.

D. Spiny-Type Nanoencapsulates

During the carbon-arc process, described above and in Example 1, a carbonaceous deposit forms on one of the graphite rods, from which the nanoencapsulates are recovered. A soot is also produced during the process, and when the anode rod is drilled out and packed with Gd, $Gd_2O_3$ or $Nd_2O_3$, a new structure has been found in the soot.

Figure 9:
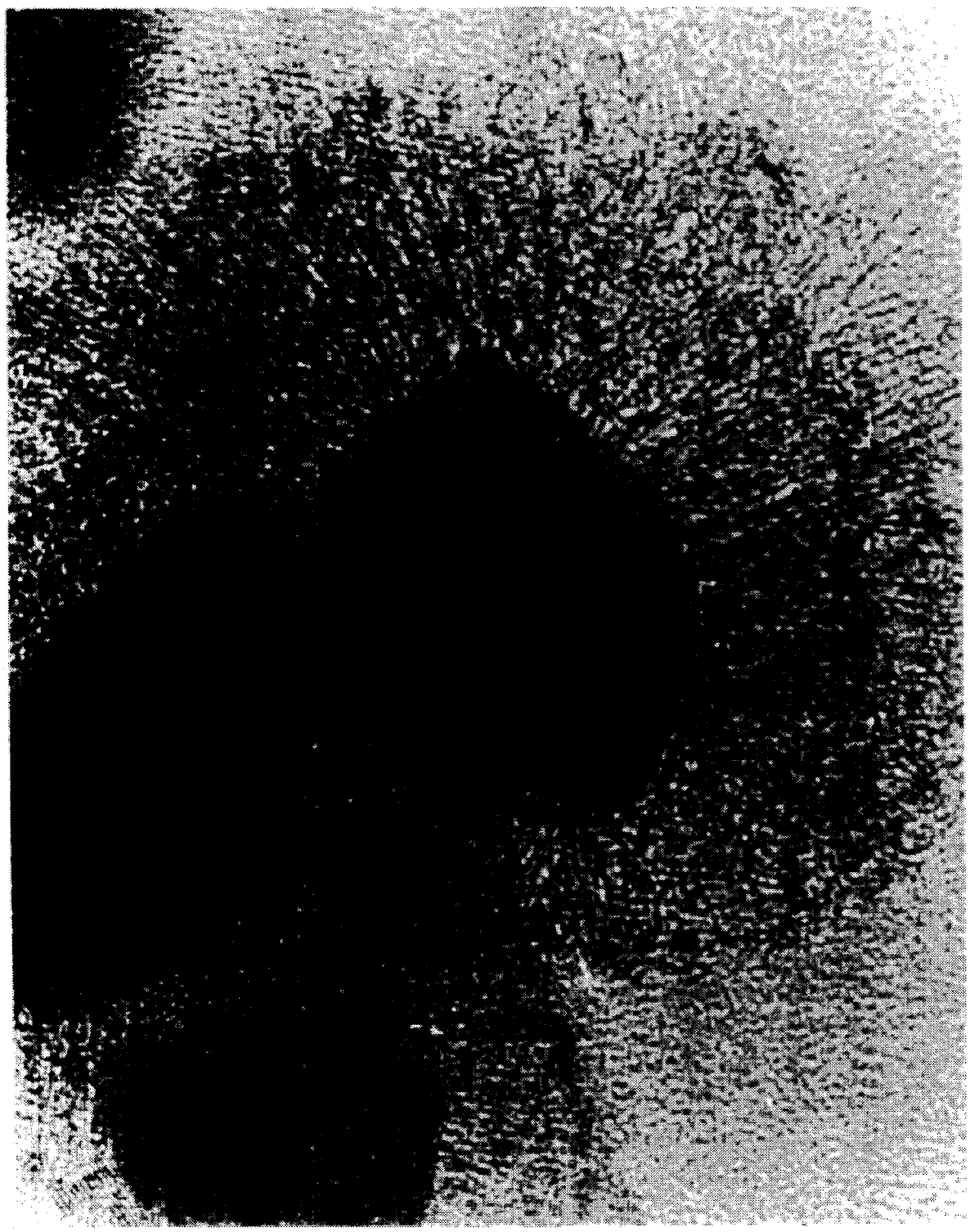
FIG. 9 is a HRTEM image of an encapsulate having a central metal core surrounded by single-wall nanotubes radiating outwards in all directions.

This structure, shown in FIG. 9, is also a nanoencapsulate and consists of an amorphous $Gd_xC_y$ core with clusters of single layer nanotubes arranged about the core, giving the appearance of spines. This structure is referred to herein as a "sea-urchin" structure of "spiny-type" nanoencapsulate. The core of the "spiny-type" nanoencapsulate seen in FIG. 9 is approximately 28 nm in diameter and the outer diameter defined by the nanotubes is approximately 90 nm.

The HRTEM image in FIG. 9 shows a central core of metal and extending radially outward from the core, a plurality of single layer carbon nanotubes. Some of these nanotubes are arranged in cylindrical clusters or bundles. Such bundles of nanotubes, where the single-layer nanotubes are on the order of <75 nm in length, can be seen in FIG. 9 and are radiating out from the central metal core. In some of the nanoencapsulates observed, some of the bundles also appear to contain multi-layer tubes.

Energy dispersive spectroscopy confirmed that the core of the "spiny-type" nanoencapsulates are Gd based compounds.

Structures similar to the "spiny-type" nanoencapsulate yet having regions with no spines have also been observed in the soot. Single crystal nuclei partially encapsulated with turbostratic carbon layers have been identified. The bundles of single layer tubes are not present on those facets where layers of turbostratic carbon cover the $\alpha$-$GdC_2$ crystals.

These "spiny-type" nanoencapsulates may have similar applications as described herein for the nanoencapsulates.

E. Applications for Nanoencapsulates

The nanoencapsulates of the present invention have numerous applications in material science, chemistry, medicine and biotechnology. In particular, the magnetic nanoencapsulates of the present invention represent a class of materials which will find applications in a wide range of fields. Encapsulated carbides and alloys unite the magnetic properties of non-organic materials with a carbon shell ideal for organic and polymer chemistry and related applications.

1. Reduce Explosiveness or Flammability of Metal Powders

One important feature of the nanoencapsulates of the present invention is that, although many of the metals used are normally sensitive to air, moisture, or both, encapsulation protects these metals from degradation by air and moisture. For example, bulk dicarbides of La, Gd, and U undergo hydrolysis. However, as discussed above, nanoencapsulates of these metals are stable and appear to not undergo such hydrolysis. A corollary to this stability is that the explosive or flammable nature of fine metal powders is essentially eliminated in nanoencapsulates preparations of metals.

2. Derivatized Nanoencapsulates

The surfaces of the nanoencapsulates of the present invention may be derivatized applying derivatization methods useful with fullerene and nanotube molecules. Numerous functional groups can be attached to the surface of the nanoencapsulates, including, but not limited to, the following: amines, hydroxyls, carboxyls, ethers, ketones and epoxides. For example, the surface of the nanoencapsulates may be derivatized with hydroxyl groups by treatment with periodate or by ozonolysis. Alternatively, nanoencapsulates may be derivatized to contain epoxides on their surfaces by exposing them to oxygen (Hoke, et al., 1992; Wood, et al., 1991; Kalsbeck, et al., 1991; Diederich, et al., 1991; Taylor, et al., 1992a; Tuinman, et al., 1992). Epoxides can be converted to form ethers using heat or ultraviolet light. Oxidation of the nanoencapsulates can be accomplished, for example, by heating them in the presence of oxygen, carbon dioxide or carbon monoxide.

Amine derivatives (Wudl) including primary amines, of the nanoencapsulates may be generated by reacting the nanoencapsulates with an amine. For example, magnetic nanoencapsulates may be separated from other carbon-arc products. To these nanoencapsulates, n-propylamine may then be added and the solution stirred at room temperature to allow the reaction to proceed. Other amine containing reagents can be used as well (for example, dodecylamine, morpholine, t-butylamine, ethylenediamine).

Grignard and organolithium reagent additions may also be carried out (Wudl, et al., 1992). The surfaces of the nanoencapsulates may be derivatized to contain halogens (e.g., C1, Br) as well (Tebbe, 1991; Olah, 1991; Birkett, 1991; Tebbe, 1992). Halogen derivatives are very useful intermediates in organic syntheses.

The nanoencapsulate derivatives described above can be further derivatized, using standard coupling reaction chemistry, to couple the nanoencapsulates and a molecule or compound of interest: for example, amino acids, peptides, polypeptides, enzymes, ribosomes, drug molecules, antibodies, avidin, biotin, nucleic acids, polymer monomers and polymers. An exemplary coupling reaction involves the use of N-hydroxysuccinimide (NHS) homobifunctional crosslinking reagents (Pierce, Rockford Ill.). The reagents react with primary amine functional groups. In the neutral to alkaline pH range the amino group reacts with the NHS ester to form a stable, amide bond. N-hydroxysuccinimide is released as a by-product.

Further, nanoencapsulates of the present invention may generally be used as a solid supports for separation and synthesis reactions (e.g., for polymer synthesis, a monomer may be coupled to nanoencapsulates and subsequent addition of further subunits to the monomer).

3. Magnetic Recording Media

The encapsulated metals of the present invention have considerable potential for uses in magneto-optical and holographic recording. Unlike many magnetic materials currently used in recording media, encapsulated magnetic crystals are corrosion-resistant, and therefore do not suffer degradation in their magnetic and electrical properties over time. Nanoencapsulates are ideal for incorporation in polymer matrices because of the minute size of the encapsulated magnetic crystals and their carbon encasement.

Figure 10:
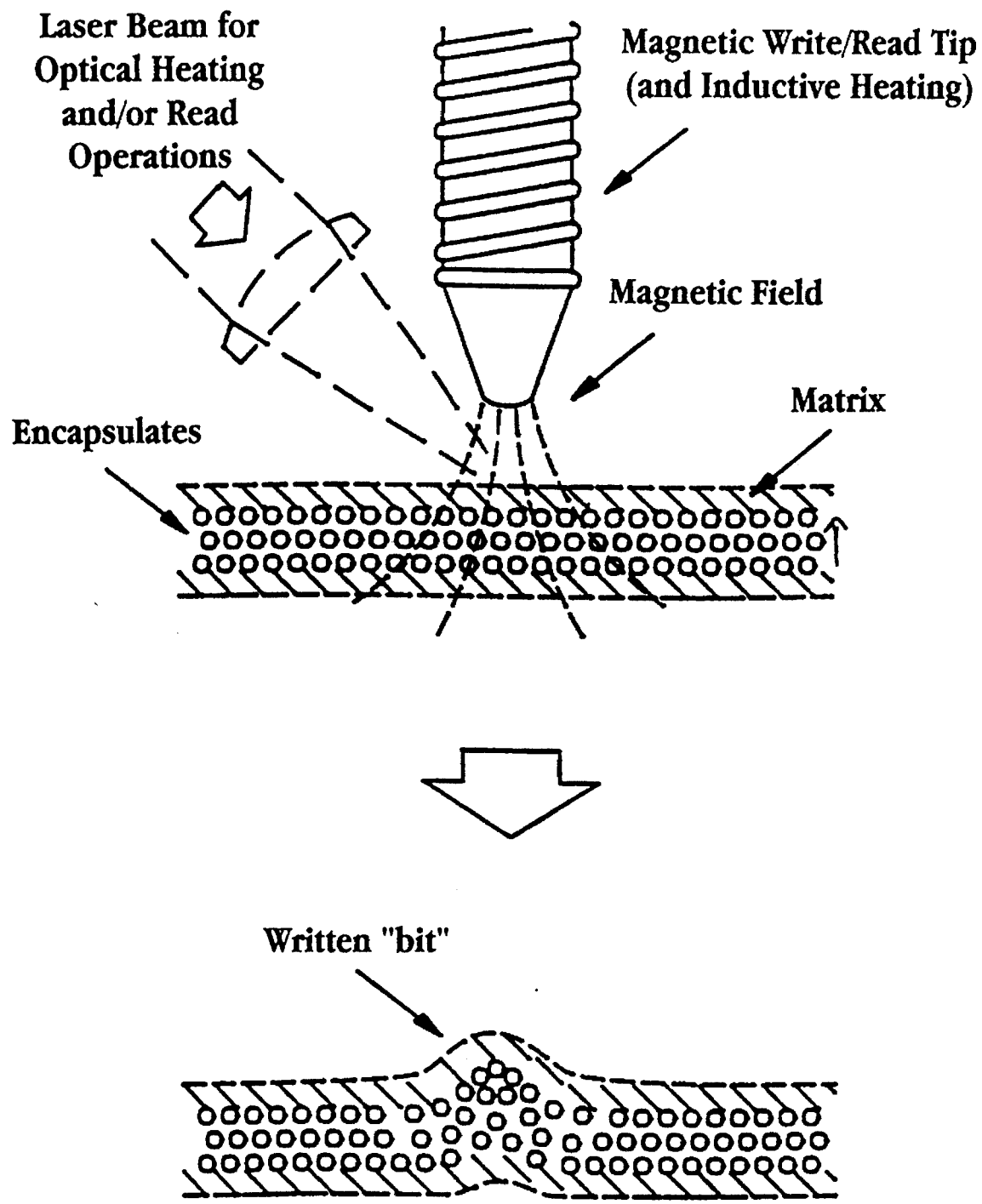
FIG. 10 illustrates a scheme for magnetic recording using magnetic nanoencapsulates of the present invention.

Discrete, carbon-encapsulated superparamagnetic materials can produce a high density coating of magnetic particles which are non-interacting and therefore do not suffer demagnetization effects from adjacent magnetic particles. FIG. 10 illustrates a scheme for magnetic recording. A diode laser, or fine tip inductive heating element, momentarily heats an area of a few square microns while a magnetic field is applied to the heated area. The area softens, is pulled out of position by the magnetic field, and forms either a pit or raised area which is then permitted to harden. The written "bit" may then be read either optically or by a magnetic force tip. Because this principle does not rely upon magnetic alignment of particles, it is insensitive to demagnetization.

The present invention contemplates production of single-domain carbon encapsulated ferromagnetic (or ferromagnetic) particles with large moments, and ellipsoidal geometry with the desirable shape anisotropy. Floppy disks in use today consist of iron oxide particles embedded in a binder, and they are designed based on this anisotropy concept. Understanding, predicting, and optimizing the magnetic characteristics of this new class of materials (nanoencapsulates) involves correlation of the size and morphologies determined using TEM and XRD and the magnetic responses they produce.

Techniques to optimize conditions for synthesis of the nanoencapsulates with most desirable stoichiometries, sizes, and morphologies include investigation of variations in parent materials, arc conditions, and post-formation processing. Magnetic measurements are used to identify promising trends. Also, information from magnetization data is used in conjunction with TEM and XRD data, to design methods for concentrating and purifying bulk quantities of encapsulated magnetic materials.

The encapsulates are also opaque, absorbing most of the light energy to which they are exposed. This technique is therefore expected to require much lower heating powers than necessary in present day rewritable magneto-optical data storage devices.

4. Fluid Mechanics and Magnetochemistry

Figure 11:
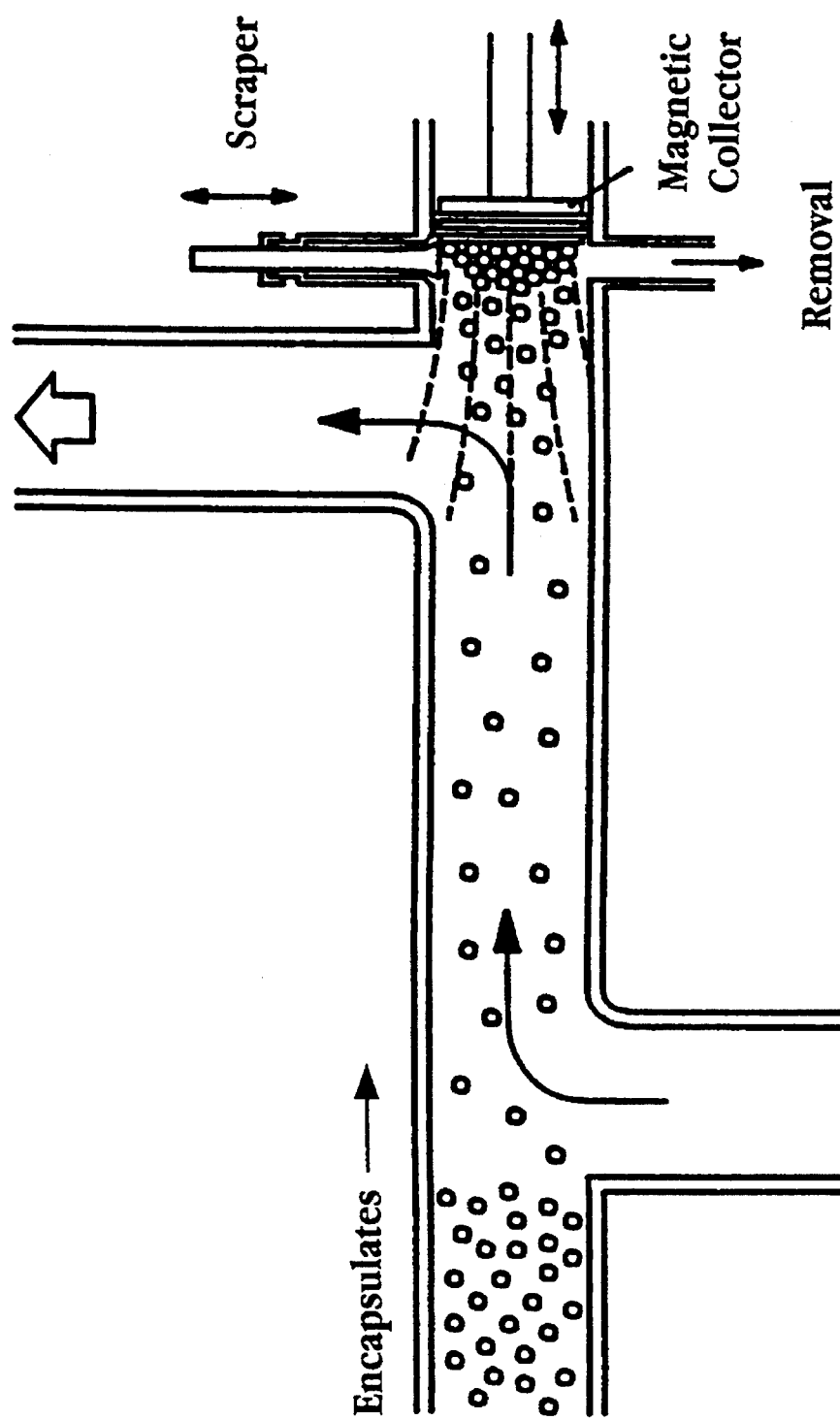
FIG. 11 illustrates a fixed magnet nanoencapsulate-reaction-platform.

Magnetic nanoencapsulates of the present invention can be manipulated or agitated independent of temperature or acoustically-induced motion (e.g., sonication) using temporally and spatially oscillating or scanning magnetic fields. The nanoencapsulates may be moved relative to their surrounding environment. Thus, a large number of encapsulates moving within a medium (e.g., liquid or gaseous) collectively represent a large surface area for reactions. This large surface area provides a high probability of contact, of any component within the medium, with a nanoencapsulate in a short period of time. Such nanoencapsulate-reaction-platforms can then be removed at any time to halt reactions or exchange for fresh encapsulates. FIG. 11 illustrates this principle.

In many inorganic and organic fluids or viscous liquids, such as petroleum derivatives, the nanoencapsulates of the present invention are expected to be readily absorbed and may be used to control reactions within such liquids. Alternatively, the nanoencapsulates can be used for the transport of pure materials into or out of reaction mixtures. Magnetic nanoencapsulates are likely to be particularly valuable in the areas of fluid mechanics and magnetochemistry.

Further, because of their small size, paramagnetic and/or ferromagnetic nanoencapsulates can be readily made airborne and circulated in a reactor or flowed along an exhaust stack to react with or adsorb unwanted contaminants. The nanoencapsulates that have reacted with such contaminants can then be removed magnetically without the need for restrictive particulate filters. This also eliminates the typical filtration stage drawbacks of clogging and filter replacement.

Figure 12:
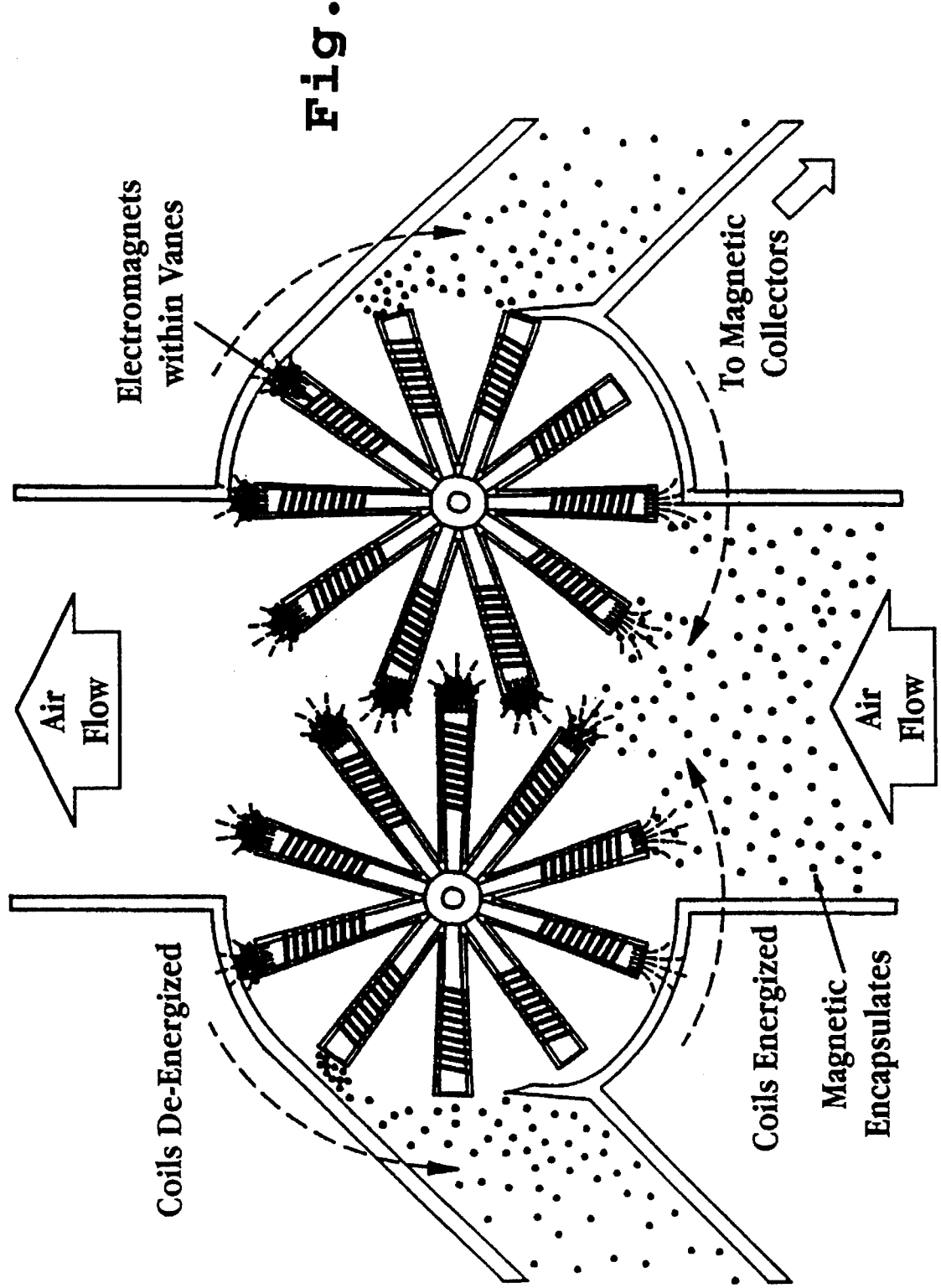
FIG. 12 illustrates magnetic filters as active components of a circulation or exhaustion system utilizing nanoencapsulates.

In applying the nanoencapsulates of the present invention to filtration, as just described, magnetic filters for the capture of nanoencapsulates may be passive, for example, using fixed permanent magnets as collectors (FIG. 11). Alternatively, the magnetic filters could be active components of a circulation or exhaustion system, such as is illustrated in FIG. 12.

5. Fuel Pellets

Nanoencapsulates of uranium have potential fuel pellet applications. Such nanoencapsulates may be useful in high temperature gas-cooled (HTGC) reactors where helium gas is typically used to cool the reactor. The reactor fuel is typically small pellets of uranium embedded in a carbonaceous matrix, such as silicon carbide (SIC). The uranium-nanoencapsulates of the present invention may provide an alternative fuel supply to the traditionally used pellets.

For example, gadolinium possesses the highest neutron absorption cross-section of any known element and the nanoencapsulates of gadolinium, in the form of gadolinium dicarbide, described herein, likely have applications in nuclear chemistry, nuclear power generation, and nuclear waste disposal.

6. Medical Uses

The nanoencapsulates of the present invention may also have applications in boron neutron capture therapy (Papaspyrou, et al.). In this embodiment, nanoencapsulates may be derivatized with a stable boron isotope (such as $^{10}B$). The derivatized nanoencapsulates are then localized to a selected tissue, organ or cell type. The targeted area is then subjected to a pure beam of cold neutrons resulting in the fission of $^{10}B$ to $^4He$ and $^7Li$: thus generating a localized concentration of alpha radiation. In one embodiment, magnetic nanoencapsulates can be derivatized with isotopic boron and localized within the body by use of an externally applied strong magnetic field.

Further, nanoencapsulates of metals (e.g., radioisotopes) used in radiation therapy (such as Yttrium, Y) may be generated and introduced into the body. The surface of these nanoencapsulates may be derivatized in order to localize the radiation to a selected tissue, organ or cell type.

7. Catalytic Uses

The nanoencapsulates have potential catalytic applications as well. The small size of the nanoencapsulates is an attractive feature for many catalytic applications. A common difficulty encountered when using finely divided metal catalysts is that they often sinter during the catalytic reaction, and lose their high activity. The graphite coating renders the nanoencapsulates non-fusible, and may therefore prevent sintering. It is also known that several metal carbides are useful catalysts for hydrodenitrogenation reactions: thus, some of these nanoencapsulates may also possess catalytic activity. In this case, the core metal may act like a dopant that modifies the surface properties of the graphite shell, which then serves to catalyze the desired reaction.

While preferred embodiments, uses, and methods of practicing the present invention have been described in detail, it will be appreciated that various other uses, formulations, and methods of practice as indicated herein are within the contemplation of the present invention.

EXAMPLE 1

Carbon-Arc Process for Synthesis of Nanoencapsulates

A. Carbon-Arc Process for Synthesis of $LaC_2$ Nanoencapsulates

A 7.9 mm diameter, 30.5 cm long graphite positive electrode was drilled to a depth of 23 mm with a 3.2 mm drill. The rod was weighed before and after packing the cavity with $La_2O_3$, to determine the La:C molar ratio of 0.02.

The $La_2O_3$ packed rod was placed in a reaction vessel along with a 12.7 mm diameter negative electrode of graphite. The rods were placed with a gap distance of 1 mm between them and this distance was maintained throughout the process by adjusting the $La_2O_3$ packed anode. Helium flowed through the vessel at a constant pressure of 500 torr and the DC current was 150 A.

The growth on the end of the cathode was collected, dispersed in ethanol by using an ultrasonic bath and deposited on carbon coated grids for transmission electron microscopy. FIG. 3A shows a HRTEM image of a nanoencapsulate, where the internal cavity of the nanopolyhedron is partially filled with $\alpha\text{-}LaC_2$.

B. Carbon-Arc Process for Synthesis of $GdC_2$ Nanoencapsulates

The procedure of Example 1A was followed except the anode was packed with $Gd_2O_3$; the gap distance was 2.5 mm, the helium pressure was 1000 Torr, and the Gd:C molar ratio was 2.3:100.

FIG. 3B is a HRTEM image of a nanoencapsulate with its inner cavity partially filled with $\alpha\text{-}GdC_2$.

$\alpha\text{-}GdC_2$ nanoencapsulates were also generated as follows. The procedure of Example 1A was followed except the anode was packed with pure Gd; the gap distance was 2.8 nm, and the Gd:C molar ratio was 8.2:100.

C. Carbon-Arc Process for Synthesis of $UC_2$ Nanoencapsulates

The procedure of Example 1A was followed except the anode was packed with uranium turnings, the gap distance was 1–3 mm, the helium pressure was 500–1000 Torr, and the U:C molar ratio was approximately 2:100.

FIG. 3C is a HRTEM image of a nanoencapsulate with its innermost cavity filled with $UC_2$.

EXAMPLE 2

X-ray Diffraction of Nanoencapsulates

Powder x-ray diffraction scans were taken on a Norelco x-ray diffraction system with microcomputer control and data acquisition and in accordance with conventional techniques. Samples were taken from the boule growth on the cathode after completion of the carbon-arc process (described in Example 1B). FIGS. 6A and 6B show XRD patterns for α-GdC$_2$ nanoencapsulates before (FIG. 6A) and after (FIG. 6B) magnetic extraction with a samarium-cobalt magnet. FIG. 6A shows the presence of α-GdC$_2$ as well as a significant amount of Gd$_2$C$_3$. The graphite seen at 26 (two-theta) degrees is primarily due to the carbon shells of the polyencapsulate. FIG. 6B, taken after exposing the sample to a gradient magnetic field, shows that α-GdC$_2$ is the component primarily extracted, as α-GdC$_2$ has a larger magnetic moment per unit mass than Gd$_2$C$_3$.

EXAMPLE 3

Magnetic Characterization of GdC$_2$ Nanoencapsulates

A computer interfaced Princeton Applied Research 4500 Vibrating Sample Magnetometer was used to measure the magnetic properties of the magnetic nanoencapsulates, such as the α-GdC$_2$ nanoencapsulates.

This apparatus is equipped with a Janis 153 liquid helium vacuum isolated cryostat for operation over the temperature range 2.5–300K and a temperature controlled oven for the range 300–1500K. The system's magnet is also computer controlled and continuously variable from −10 to +10 KOe. The sample temperature is regulated by a Lakeshore Cryotronics temperature controller, a carbon glass thermometer, and a heating element. Gaseous helium within the chamber thermally couples the vibrating sample to the carbon glass thermometer. A second temperature sensor, a chromel/gold-iron thermocouple threaded inside the sample probe allows more accurate temperature measurements. The magnetometer has a sensitivity range of $1\times10^{-5}$ to $1\times10^3$ emu.

FIGS. 7A and 7B show the magnetic moment as a function of external field for α-GdC$_2$ nanoencapsulates before (FIG. 7A) and after (FIG. 7B) separation with a magnet. These figures show that the dependence of the magnetic moment on an external field is linear with a positive slope over the entire field, which demonstrates that the α-GdC$_2$ nanoencapsulates are paramagnetic. Magnetic extraction resulted in a 20-fold increase in the concentration of this paramagnetic component, as seen in comparing the magnetic moment values in emu/gram of FIGS. 7A and 7B.

Temperature dependent magnetic moment data for the α-GdC$_2$ nanoencapsulates over the range 4 to 300K is shown in FIG. 8. A clear antiferromagnetic transition temperature at 42K is not observed for the α-GdC$_2$ nanoencapsulates. The nanoencapsulates follow the Curie law dependence on reciprocal temperature down through the transition temperature of 42K, and are thus considered to be superparamagnetic.

Although the invention has been described with respect to particular embodiments, it will be apparent to those skilled in the art that various changes and modifications can be made without departing from the invention.

It is claimed:

1. A nanoencapsulate composition, comprising;
   a metal encapsulated in a nanopolyhedron characterized by (i) an outer shell of nested, concentric layers of carbon, said shell defining an internal cavity and (ii) encapsulated in said cavity, the metal.
2. The composition of claim 1, where the outer diameter of the nanoencapsulate is between 5 nm and 1000 nm.
3. The composition of claim 1, where the outer diameter of the nanoencapsulate is between 10 nm and 500 nm.
4. The composition of claim 1, where the outer diameter of the nanoencapsulate is reduced by controlled oxidation.
5. The composition of claim 1, where the metal is from the group consisting of the actinides.
6. The composition of claim 5, where the metal is uranium.
7. The composition of claim 1, where the metal is from the group consisting of the lanthanides.
8. The composition of claim 7, where the metal is from the group consisting of La and Gd.
9. The composition of claim 1, where the composition is paramagnetic and the metal is normally ferromagnetic.
10. The composition of claim 9, where the metal is Gd.
11. The composition of claim 1, where the composition is paramagnetic and the metal is paramagnetic.
12. The composition of claim 1, where the composition is ferromagnetic and the metal is ferromagnetic.
13. The composition of claim 12, where the metal is selected from the group consisting of iron, nickel and cobalt.
14. The composition of claim 1, where the metal is an alloy.
15. The composition of claim 14, where the alloy is samarium-cobalt.
16. The composition of claim 1, where the carbon shell is derivatized with at least one molecule.

* * * * *